United States Patent
Gupta et al.

(10) Patent No.: US 9,572,777 B2
(45) Date of Patent: Feb. 21, 2017

(54) TOPICAL PHARMACEUTICAL COMPOSITION COMPRISING NANONIZED SILVER SULFADIAZINE

(71) Applicant: SUN PHARMACEUTICAL INDUSTRIES LIMITED, Mumbai, Maharashtra (IN)

(72) Inventors: Neeta Gupta, Gurgaon (IN); Simrata Bedi, Gurgaon (IN); Jyoti Srivastava, Gurgaon (IN); Vinod Kumar Arora, Gurgaon (IN); Manisha Pandya, Gurgaon (IN); Vyas M. Shingatgeri, Gurgaon (IN); Jaiprakash Jaysingrao Bhelonde, Gurgaon (IN); Monika Obrah, Gurgaon (IN); Sanjay Kumar Sharma, Gurgaon (IN); Rajinder K. Jalali, Gurgaon (IN); Sudershan Kumar Arora, Gurgaon (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 15/090,985

(22) Filed: Apr. 5, 2016

(65) Prior Publication Data

US 2016/0213712 A1 Jul. 28, 2016

Related U.S. Application Data

(63) Continuation of application No. 13/762,792, filed on Feb. 8, 2013, which is a continuation-in-part of application No. 13/814,086, filed as application No. PCT/IB2011/053263 on Jul. 21, 2011.

(30) Foreign Application Priority Data

Aug. 2, 2010 (IN) ............................ 1821/DEL/2010
Aug. 30, 2012 (IN) ............................ 2690/DEL/2012

(51) Int. Cl.
A61K 39/108 (2006.01)
A61K 9/14 (2006.01)
A61K 33/38 (2006.01)
A61K 9/00 (2006.01)
A61K 31/155 (2006.01)
A61K 31/555 (2006.01)
A61K 31/635 (2006.01)

(52) U.S. Cl.
CPC .............. *A61K 9/14* (2013.01); *A61K 9/0014* (2013.01); *A61K 31/155* (2013.01); *A61K 31/555* (2013.01); *A61K 31/635* (2013.01); *A61K 33/38* (2013.01)

(58) Field of Classification Search
CPC ........ A61K 9/14; A61K 33/38; A61K 9/0014; A61K 31/155; A61K 31/555; A61K 31/635
See application file for complete search history.

(56) References Cited

U.S. PATENT DOCUMENTS

| 3,761,590 A | 9/1973 | Fox, Jr. ......................... 424/228 |
| 6,987,133 B2 | 1/2006 | Chen .......................... 514/772.4 |
| 8,436,050 B2 | 5/2013 | Modak et al. ................. 514/642 |
| 2003/0082225 A1 | 5/2003 | Mason .......................... 424/449 |

FOREIGN PATENT DOCUMENTS

| BE | 892421 | 7/1982 | |
| CN | 1970633 | 5/2007 | ............. B29C 35/02 |
| DE | 2804931 | 8/1979 | ........... C07D 239/44 |
| EP | 0 326 145 | 8/1989 | ........... A61K 31/505 |
| FR | 2424740 | 11/1979 | ............... A61K 9/14 |
| JP | 53-44615 | 4/1978 | ........... C07D 239/44 |
| WO | WO 89/11850 | 12/1989 | ............... A61K 9/52 |
| WO | WO 2010/036945 | 4/2010 | ............. A61K 39/02 |

OTHER PUBLICATIONS

Nesamony and Kolling, "IPM/DOSS/Water Microemulsions as Reactors for Silver Sulfadiazine Nanocrystal Synthesis", *Journal of Pharmaceutical Sciences*, 94(6):1310-1320 (2005).
Silverex from Ranbaxy (Consumer HC) [Silver Sulfadiazine] [online]. Available from: http://www.drugsupdate.com/brand/generic/silver%20sulfadiazine/3375 [accessed May 25, 2012].
Indian Patent Application No. IN 1038/KOL/2005, filed on Nov. 18, 2005, entitled "A therapeutic composition for treating burn injury/lesions resulting therefrom, and process for preparing the same."

*Primary Examiner* — Nannette Holloman

(57) ABSTRACT

The invention relates to a topical pharmaceutical composition for burn treatment and microbial infections on human beings or animals. The pharmaceutical composition comprises 0.1% w/w to 1.0% w/w of an antimicrobial drug, i.e., silver sulfadiazine and 0.2% w/w antiseptic, i.e., chlorhexidine gluconate, wherein silver sulfadiazine is in nanonized form.

11 Claims, No Drawings

TOPICAL PHARMACEUTICAL COMPOSITION COMPRISING NANONIZED SILVER SULFADIAZINE

FIELD OF THE INVENTION

The present invention relates to a topical pharmaceutical composition for burn treatment and microbial infections on human beings or animals. The pharmaceutical composition comprises 0.1% w/w to 1.0% w/w of an antimicrobial drug, i.e., silver sulfadiazine and 0.2% w/w antiseptic, i.e., chlorhexidine gluconate, wherein silver sulfadiazine is in nanonized form.

BACKGROUND OF THE INVENTION

Silver sulfadiazine was first described in 1943 by Wruble and was found to be mildly antiseptic. U.S. Pat. No. 3,761,590 describes a process for preparing a thick cream ointment containing silver sulfadiazine, which rejuvenated the compound for the topical treatment of burns. The 1% w/w of this active drug, in the form of a cream, has been in clinical use in the USA since 1973.

Chlorhexidine is a bisbiguanide antiseptic and disinfectant effective against a wide variety of bacteria, some fungi, and some viruses. It is used clinically in various preparations for disinfecting purposes.

The antimicrobial effect of silver sulfadiazine and chlorhexidine compounds has been clinically established. It has been well known that silver sulfadiazine is effective against a wide variety of gram-positive and gram-negative organisms, including *Pseudomonas* and *Candida*.

The prior art discloses a number of formulations of silver sulfadiazine for treatment of burns.

European Publication No. 0 326 145 discloses a composition for the topical treatment of herpes infections, varicella, eczema, and burns ($2^{nd}$ and $3^{rd}$ degree) comprising 0.01% w/w to 10% w/w silver sulfadiazine, 0.01% w/w to 10% w/w polyhydric alcohol, and optionally a local anesthetic.

Belgian Patent No. 892,421 relates to stable ointments and lotions containing silver sulfadiazine and a hydrophilic excipient for the treatment of mucosal infections without causing irritation.

French Patent No. 2,424,740 describes lotions, ointments, and powders containing finely divided silver sulfadiazine or zinc sulfadiazine. These salts were prepared in situ from sodium sulfadiazine. A lotion was prepared by dissolving sodium sulfadiazine in water, homogenizing with Tween® 80, paraffin, isopropyl palmitate, sorbitan monooleate, Myrj® 52, and stearyl alcohol. The mixture was homogenized with silver nitrate in water at 3000 rpm to form finely divided silver sulfadiazine with a particle size of <5 μm, and with 90% of particles <0.7 μm.

Indian Patent Application No. 1038/KOL/2005 relates to a therapeutic composition for treating burn injury and lesions, comprising the following active ingredients in the amounts given below (a) sucralfate—1% w/w to 8% w/w; (b) silver sulfadiazine—0.5% w/w to 2% w/w; and (c) chlorhexidine gluconate—0.1% w/w to 0.3% w/w, in admixture with pharmaceutically acceptable excipients, adjuvants, fillers, humectants and/or stabilizers. It also relates to a process for preparing the above-mentioned therapeutic composition for burn wound management.

U.S. Pat. No. 6,987,133 discloses a topical spray preparation for burn treatment comprising silver sulfadiazine dispersed or solubilized in the cream or lotion base matrix, which can be sprayed directly from a common trigger spray device.

Commercial formulations containing chlorhexidine gluconate 0.2% w/w, and silver sulfadiazine 1% w/w, e.g., Silvazine®, Nisburn®, or Silverex® cream, are available in the market; however, the particle size range of silver sulfadiazine in these formulations is in the micronized range.

The activity of silver sulfadiazine, in the cream form, may be influenced by the following factors:
 (a) the release rate of the active ingredient from the cream matrix into the wound environment;
 (b) particle size and solubility of the active ingredient in the fluids of the wound; and
 (c) stability of the active ingredient in the cream matrix.

Among these factors, particle size is one of the most critical parameters which affects the solubility and release of the active ingredient from the pharmaceutical composition at the wound site. Smaller particle size will lead to increased antimicrobial effectiveness. Therefore, further size reduction of silver sulfadiazine particles as compared to the marketed micronized product may result in greater antimicrobial effectiveness based on enhanced solubility of silver sulfadiazine. However, this size reduction may lead to stability concerns as well.

Particle size reduction to improve the drug performance has long been known and used in the pharmaceutical industry. Nanonization, i.e., particle size reduction to the nanosize range is a known technique for improving the solubility of the active ingredient, thereby leading to improved absorption and better therapeutic efficacy. However, the selection of the optimum particle size range as well as the selection of the method for particle size reduction remains critical for the chosen active drug. Further, achieving the desired stability throughout the shelf life is equally important.

Nesamony et al, in their article entitled "IPM/DOSS/Water Microemulsions as Reactors for Silver Sulfadiazine Nanocrystal Synthesis", published in Journal of Pharmaceutical Sciences, Volume 94, No. 6, pp. 1330-1320 (2005), have disclosed a method of preparing silver sulfadiazine nanocrystals in situ by mixing sodium sulfadiazine and silver nitrate using a microemulsion technique. The silver sulfadiazine nanocrystals so prepared have a particle size of ~670 nm, as measured by laser diffraction technique. Preparation of nanocrystals using microemulsion technique is a complex process.

There still remains a need for a topical pharmaceutical composition comprising nanonized silver sulfadiazine demonstrating improved efficacy over the already marketed product.

The object of the present invention is to provide a topical pharmaceutical composition comprising an antimicrobial drug, i.e., silver sulfadiazine in a weight ratio of 0.1% w/w to 1.0% w/w and an antiseptic, i.e., chlorhexidine gluconate in a weight ratio of 0.2% w/w, wherein silver sulfadiazine is in nano-size range. The pharmaceutical composition of the present invention is advantageous over the currently available micronized products in having improved efficacy, thereby leading to dose reduction as well as faster wound healing due to quicker absorption of nanonized particles having increased surface area. Also, no significant increase in toxicity was observed as a result of size reduction. The inventors were able to obtain a stable pharmaceutical composition of silver sulfadiazine having nanonized particles of silver sulfadiazine. The compositions of the invention comprising 0.5% w/w and 0.75% w/w nanonized silver sulfadiazine have comparable efficacy to the 1.0% w/w marketed product (micronized silver sulfadiazine) in patients with partial thickness thermal burns. Comparable efficacy provides significant dose reduction to a patient in need of silver sulfadiazine for burn treatment. The composition containing 1.0% w/w nanonized silver sulfadiazine shows greater efficacy than the 1.0% w/w marketed product (micronized silver sulfadiazine).

SUMMARY OF THE INVENTION

The present invention relates to a topical pharmaceutical composition comprising 0.1% w/w to 1.0% w/w silver sulfadiazine, 0.2% w/w chlorhexidine gluconate, and one or more pharmaceutically acceptable excipients, wherein silver sulfadiazine has a Z-average particle size between 150 nm and 500 nm.

According to one of the aspects of the present invention, there is provided a topical pharmaceutical composition of nanonized silver sulfadiazine having a Z-average particle size between 150 nm and 500 nm, wherein the dose of silver sulfadiazine is reduced from 1.0% w/w to 0.5% w/w to 0.75% w/w without change in efficacy, when the composition containing nanonized silver sulfadiazine is compared to the composition containing micronized silver sulfadiazine.

According to another aspect of the present invention, there is provided a topical pharmaceutical composition of nanonized silver sulfadiazine having a Z-average particle size between 150 nm and 500 nm, wherein the dose of silver sulfadiazine is reduced from 1.0% w/w to 0.5% w/w to 0.75% w/w without change in efficacy, when the composition containing nanonized silver sulfadiazine is compared to the composition containing micronized silver sulfadiazine and the efficacy is determined by:
  (a) proportion of patients achieving complete wound closure by day 21 of the treatment period; or
  (b) microbial log reduction of *Pseudomonas aeruginosa* count in thermal injury model in rats.

According to yet another aspect, there is provided a topical pharmaceutical composition of 0.5% w/w to 0.75% w/w nanonized silver sulfadiazine having a Z-average particle size between 150 nm and 500 nm, wherein application of said composition to patients leads to complete wound closure by day 21 of the treatment period in at least 90% of the total patient population.

According to another aspect of the present invention, there is provided a topical pharmaceutical composition of 0.5% w/w to 0.75% w/w nanonized silver sulfadiazine having a Z-average particle size between 150 nm and 500 nm, wherein the microbial log reduction of *Pseudomonas aeruginosa* count in thermal injury model in rats using said composition is comparable to that caused by the composition containing 1.0% w/w micronized silver sulfadiazine.

According to a further aspect of the present invention, there is provided a topical pharmaceutical composition of 1.0% w/w nanonized silver sulfadiazine having a Z-average particle size between 150 nm and 500 nm, wherein the microbial log reduction of *Pseudomonas aeruginosa* count in thermal injury model in rats using said composition is greater than that caused by the composition containing 1.0% w/w micronized silver sulfadiazine.

According to yet another aspect of the present invention, there is provided a topical pharmaceutical composition comprising 0.1% w/w to 1.0% w/w silver sulfadiazine having a Z-average particle size between 150 nm and 500 nm, wherein the said composition further comprises pharmaceutically acceptable excipients selected from one or more of thickening agents, emulsifying agents, preservatives, chelating agents, pH modifiers, coloring agents, perfumes, and antioxidants.

DETAILED DESCRIPTION OF THE INVENTION

This invention relates to a pharmaceutical composition for topical application to treat burn wounds and infections, wherein silver sulfadiazine is in the nanonized form.

The pharmaceutical composition for topical application may be in the form of a cream, lotion, ointment, or gel.

The pharmaceutical composition comprises an antimicrobial drug and an antiseptic as the active ingredients. The antimicrobial drug as used herein is silver sulfadiazine in a concentration of 0.1% w/w to 1.0% w/w and the antiseptic is chlorhexidine gluconate in a concentration of 0.2% w/w. Silver sulfadiazine is dispersed and chlorhexidine gluconate is solubilized in a cream or lotion base, wherein silver sulfadiazine is in nanonized form.

The term "nanonized" as used herein refers to a Z-average particle size of less than or equal to 600 nm, e.g., Z-average particle size between 150 nm and 500 nm. The Z-average particle size is the mean diameter based on the intensity of light scattered, as determined using a Nanosizer or Zetasizer, based on the principle of dynamic light scattering.

Polydispersity Index (PI), an indicator of the spread in particle size, is a parameter also available using a Nanosizer or Zetasizer. The PI value for silver sulfadiazine in the nanonized formulation is between 0.4 and 0.8, for example 0.5 to 0.6.

In particular, the Z-average particle size of the nanonized silver sulfadiazine used in the compositions of the invention was found to be 277 nm, 314 nm, 347 nm, 359 nm, or 465 nm.

Nanonization is a size reduction technique that leads to an increased particle surface area and thus increased dissolution velocity, which in turn leads to faster absorption. Enhanced absorption leads to improved efficacy thereby leading to substantial dose reduction. Also, in the present case, no significant increase in toxicity was observed as a result of size reduction.

Efficacy of the composition was determined by the following parameters: a) proportion of patients achieving complete wound closure by day 21 of the treatment period; or b) microbial log reduction of *Pseudomonas aeruginosa* count in thermal injury model in rats.

Details of the clinical studies demonstrating the difference in wound closure in patients treated with different concentrations of nanonized and micronized silver sulfadiazine are given under the heading 'Clinical Study'. The compositions comprising 0.5% w/w and 0.75% w/w of nanonized silver sulfadiazine cream clearly provided better results in comparison with 1.0% w/w micronized silver sulfadiazine. Complete wound closure on day 21 of the treatment period was achieved in 11 out of 12 (91.7%) subjects in the 0.5% w/w nanonized silver sulfadiazine group; 11 out of 11 (100%) subjects in the 0.75% w/w nanonized silver sulfadiazine group and 6 out of 11 (54.5%) subjects in the 1.0% w/w micronized silver sulfadiazine group. Therefore, nanonization has led to dose reduction and also reduced time of treatment and enhanced healing in patient population.

The efficacy of silver sulfadiazine nanonized cream against *Pseudomonas aeruginosa* was determined in the mouse superficial skin model with burn wound infection caused by thermal injury. Microbial log reduction of *Pseudomonas aeruginosa* count was determined on day 15.

Details are provided later under the heading 'Animal model studies.' Silver sulfadiazine nanonized (SSN) 1.0% w/w cream leads to greater log reduction in the *Pseudomonas aeruginosa* count as compared to the marketed product Silverex® 1.0% w/w. (The microbial log reduction using 0.5% w/w and 0.75% w/w silver sulfadiazine nanonized cream is found to be similar to the marketed 1.0% w/w Silverex®.)

Based on these findings, the lower strength silver sulfadiazine (nanonized), i.e. 0.5% w/w or 0.75% w/w, may be used for patients with an aim of reducing the dose.

Topical compositions of silver sulfadiazine may be formulated using standard techniques known in the industry. For example, such formulations may be produced as oil-in-water or water-in-oil emulsions using suitable proportions of a hydrophobic phase with the addition of a thickening agent and a hydrophilic phase. Such formulations include, in general, one or more of emulsifying agents, preservatives, chelating agents, pH modifiers, antioxidants, or fragrance/perfumes.

Such hydrophobic phases may include mineral oils such as liquid paraffin or a vegetable oil such as peanut oil or castor oil.

Thickening agents which may be used according to the characteristics of the base may include, for example, soft paraffin, aluminum stearate, cetostearyl alcohol, propylene glycol, polyethylene glycols, polyvinyl pyrrolidone, wool-fat, hydrogenated lanolin, beeswax, or a mixture thereof.

A suitable emulsifying agent may be selected from one or more of cetomacrogol, non-ethoxylated glyceryl monostearate, carbopols, cetearyl alcohol, sodium stearoyl lactylate, or lecithin.

A suitable preservative is one or any combination selected from the group consisting of methylparaben, propylparaben, benzyl alcohol, benzoic acid, sodium benzoate, chlorocresol, sorbic acid and its salt, or phenylethyl alcohol.

Suitable chelating agents may be selected from one or more of dimercaprol, ethylene diamine tetra acetic acid (EDTA), disodium edetate, ethylene glycol tetraacetic acid, deferoxae, or alfa lipoic acid.

Suitable pH modifiers may be selected from one or more of citric acid, sodium citrate, acetic acid, sodium acetate, phosphoric acid, sodium phosphate, borax, or sodium hydroxide.

Silver sulfadiazine is prone to oxidation, thereby causing the nanonized slurry to turn black on exposure to the environment during the milling process. This instability problem is more pronounced in the case of the nanonized product (due to increased surface area) as compared to the already marketed micronized product. The addition of suitable antioxidants is useful in overcoming the instability problem.

The antioxidant used in the present invention may be selected from hydrogen peroxide, sodium metabisulfite, butylated hydroxytoluene, butylated hydroxyanisole, propyl gallate, ethyl gallate, methyl gallate, ascorbic acid, tocopherol, or a mixture thereof.

According to one embodiment of the invention, the topical pharmaceutical composition contains a combination of butylated hydroxytoluene, hydrogen peroxide, and sodium metabisulfite for use as antioxidants.

The present invention also relates to a method of preparation of the nanonized topical pharmaceutical composition of silver sulfadiazine, the process steps comprising of:

(a) dispersing a thickening agent, chelating agent, and one or more pharmaceutically acceptable excipients in water to form a slurry;

(b) adding and mixing silver sulfadiazine in the slurry of step (a);

(c) charging the slurry in a Dynomill and unloading after the particle size of silver sulfadiazine in the slurry is in the nanonized range;

(d) preparing the oily phase by mixing together one or more hydrophobic bases and heating the mixture to obtain a molten mass;

(e) preparing the aqueous phase by heating purified water and optionally dissolving a preservative in it;

(f) slowly adding the oily phase of step (d) to the aqueous phase of step (e) and homogenizing to form an emulsion;

(g) adding and mixing silver sulfadiazine slurry of step (c) into the bulk of step (f);

(h) adding chlorhexidine gluconate to the cooled bulk of step (g); and (i) adjusting the pH to between 5.0 and 6.5 using one or more pH modifiers and finally adjusting the weight using purified water and mixing.

Animal Model Studies

The improved efficacy of the nanonized pharmaceutical composition of the present invention has been demonstrated by in vivo efficacy studies in the burn wound infection model by comparing the log reduction of *Pseudomonas aeruginosa* using various concentrations of nanonized silver sulfadiazine to untreated control, commercially available Silverex® (1.0% w/w micronized silver sulfadiazine), and levofloxacin therapy. Swiss albino mice were put into six groups and their backs were shaven. Thermal injury was induced in the shaven area by applying a heated brass rod on the back of the animals for 15 seconds to 20 seconds. For establishment of a topical infection, an inoculum containing approximately $2 \times 10^5$ bacteria (*Pseudomonas aeruginosa*) was injected subcutaneously (100 µL) on the sites of the burns. One hour post infection, the mice were treated using 100 mg of cream formulations of different drug concentrations. In case of all the cream formulations, 100 mg cream was applied topically twice daily for 5 days. One of the groups of mice was given Levofloxacin orally at 25 mg/kg body weight as a reference standard.

The results of the efficacy of silver sulfadiazine nanonized cream against *Pseudomonas aeruginosa* in mouse superficial skin model caused by thermal injury, on day 6 have been shown in Figure 1 and Table 1.

TABLE 1

| Log reduction of microbial count | |
| --- | --- |
| Silver sulfadiazine nanonized cream 0.5% w/w | 1.85 $\log_{10}$ |
| Silver sulfadiazine nanonized cream 0.75% w/w | 1.17 $\log_{10}$ |
| Silver sulfadiazine nanonized cream 1.0% w/w | 3.14 $\log_{10}$ |
| Silverex ® 1.0% w/w | 2.15 $\log_{10}$ |
| Levofloxacin (25 mg/kg body weight) | 5.53 $\log_{10}$ |

As seen from the results of the in vivo efficacy studies, 1.0% w/w silver sulfadiazine nanonized (SSN) cream leads to greater log reduction in the *Pseudomonas aeruginosa* count in the mouse superficial skin model caused by thermal injury as compared to the marketed product Silverex® 1.0% w/w. (The microbial log reduction using 0.5% w/w silver sulfadiazine nanonized cream is found to be similar to the marketed 1.0% w/w Silverex®.)

To further evaluate the efficacy of silver sulfadiazine (nanonized) cream in thermal injury model in male sprague dawley rats after application of the cream once daily for 15 consecutive days, histopathological evaluation of the tissue samples from the site of injury was carried out. The microscopic lesions were evaluated for necrosis, inflammatory cells, immature granulation tissue, mature granulation tissue, fibrosis, and re-epithelization to interpret the various wound healing events.

Marked to severe necrosis was observed in all of the animals belonging to different treatment groups including the control, indicating the accuracy and precision of the thermal injury process. Hence, necrosis in the present study is not a measure of the wound healing process. The animals were grouped in five sets, namely Groups I-V. Group I consisted of untreated control; Group II were treated with 0.5% w/w nanonized silver sulfadiazine (SSN); Group III with 0.75% w/w SSN; Group IV with 1.0% w/w SSN; and Group V were treated with micronized Silverex® 1.0% w/w.

The mean score of inflammation (i.e. presence of inflammatory cells) was very low in Group II animals (0.5% w/w SSN) compared with Group I (control) and other treatment Groups III (0.75% w/w SSN), IV (1.0% w/w SSN), and V (1.0% w/w Silverex®). Similarly, the mean scores of granulation tissue (immature, mature, and fibrosis) was low in Group II animals (0.5% w/w SSN) compared with Group I (control) and other treatment Groups III (0.75% w/w SSN), IV (1.0% w/w SSN) and V (1.0% Silverex®).

The re-epithelization (expressed as percent closure of wound by newly forming squamous cells) was high in Group II animals (0.5% w/w SSN) followed by Group III (0.75% w/w SSN), Group IV (1.0% w/w SSN) and Group V (1.0% Silverex®).

Table 2, 3, and 4 present the mean histopathological scores of various wound healing parameters studied in the present study.

TABLE 2

Mean Histopathology Score of Healing Parameters

| Group | Wound Healing Parameters | | | | | |
|---|---|---|---|---|---|---|
| | Necrosis | Inflammatory cells | Immature GT | Mature GT | Fibrosis | Re-epithelization |
| I | 4.4 | 2.9 | 2.1 | 1.4 | 1.1 | 22.5 |
| II | 4.6 | 1.3 | 1.7 | 0.9 | 1.1 | 41.0 |
| III | 4.8 | 1.7 | 1.8 | 0.8 | 1.4 | 28.5 |
| IV | 4.5 | 1.5 | 1.4 | 1.0 | 1.3 | 27.0 |
| V | 4.7 | 2.4 | 2.0 | 1.1 | 0.5 | 31.0 |

TABLE 3

Summary of Reepithelization (%) Scores

| Re-epithelization Score | Group I | Group II | Group III | Group IV | Group V |
|---|---|---|---|---|---|
| ≤5% | 4 | 2 | 3 | — | 2 |
| ≤10% | 3 | 3 | 1 | 5 | 2 |
| ≤25% | 1 | 1 | 1 | 2 | 2 |
| ≤50% | — | — | 3 | 1 | 1 |
| ≤75% | 1 | — | 2 | 1 | 2 |
| ≤100% | 1 | 4 | — | 1 | 1 |

TABLE 4

Summary of Inflammatory Cells

| Inflammatory Cells Score | Group I | Group II | Group III | Group IV | Group V |
|---|---|---|---|---|---|
| 0.5 (very minimal) | — | 3 | — | — | — |
| 1 (minimal) | — | 2 | 4 | 5 | 6 |
| 2 (mild) | 4 | 5 | 5 | 5 | 4 |
| 3 (moderate) | 3 | — | 1 | — | — |
| 4 (marked) | 3 | — | — | — | — |

Overall, all the healing parameters viz. inflammation, granulation tissue, and re-epithelization evaluated in the present study showed improved results in animal groups treated with nanonized silver sulfadiazine formulation when compared with the untreated control group and the group treated with 1.0% w/w Silverex®.

Pharmacokinetic Studies

The plasma exposures of silver and sulfadiazine were determined on day 15 following once daily application of different strengths of silver sulfadiazine (nanonized) cream as test items (SSN 0.5% w/w; 0.75% w/w; and 1.0% w/w) and Silverex® cream 1.0% w/w (as reference item). Sulfadiazine was quantified by LC-MS/MS method. The mouse plasma samples were analyzed by API 4000 QTRAP MS/MS detector in positive ion mode using a Kromasil C18, (100×4.6 mm), 3.5µ column. The mobile phase used was acetonitrile:water:formic acid (80:20:0.05) at a flow rate of 0.6 mL/minute.

Silver concentrations were estimated using an ICPMS instrument (Inductively Coupled Plasma—Mass Spectrometry). The conditions for ICPMS employed were: silver with 107 amu, an injection volume of about 1 mL, with the carrier gas flow rate of 0.95 l/minute/minute; make-up gas flow rate of 0.2 l/minute; and plasma gas flow rate of 15 l/minute. The readings were taken in replicates of three.

The pharmacokinetic parameters for test and reference items are given in Table 5.

TABLE 5

Pharmacokinetic parameter values for Silver and Sulfadiazine

| Formulation | $C_{max}$ (µg/mL) | | $AUC_{0-t}$ (h * µg/mL) | |
|---|---|---|---|---|
| | Silver | Sulfadiazine | Silver | Sulfadiazine |
| Silverex ®-1.0% | 0.22 | 27.63 | 3.88 | 493.56 |
| SSN-0.5% | 0.14 | 16.71 | 2.44 | 254.47 |
| SSN-0.75% | 0.14 | 19.99 | 3.02 | 361.74 |
| SSN-1.0% | 0.21 | 34.52 | 4.68 | 541.95 |

The $C_{max}$ of sulfadiazine for different SSN formulation prototypes increased from 16.71 µg/mL to 34.52 µg/mL with the increase in strengths from 0.5% w/w to 1% w/w. Similarly, the AUC increased from 254.47 h*µg/mL to 541.95 h*µg/mL with the increase in SSN strengths. The AUC ratio (Test/Reference) ranged from 0.52 to 1.10 after 15 days of dermal application.

The AUC of silver was calculated from silver concentrations of pooled plasma samples. The exposure of silver also increased from 2.44 h*µg/mL to 4.68 h*µg/mL with the increase in strengths of SSN creams from 0.5% w/w to 1.0% w/w. The AUC ratio (Test/Reference) ranged from 0.63 to 1.21 after 15 days of dermal application.

Both silver and sulfadiazine were found to be absorbed from the topical application of silver sulfadiazine creams in rat. The systemic exposure of both of the components (silver and sulfadiazine) was comparable to 1.0% w/w test and reference product and dose dependent for SSN after topical application for 15 days.

The silver component from nanonized silver sulfadiazine with their large surface areas and reduced particle size provide improved contact and penetration into the bacterial cell, which together enhances its antimicrobial activity. The anti-inflammatory effects of silver sulfadiazine depend on the concentration of silver at the site, release of silver from the carrier and species of silver used. To establish the safety of the size-reduced nanonized composition, toxicity studies were carried out in animal models.

Toxicity Study

This study was conducted to evaluate the toxicity profile, the target organs of toxicity, reversibility of toxicity (if any), the systemic exposure, and to determine the No Observed Effect Level (NOEL) or No Observed Adverse Effect Level (NOAEL) in Wistar Hannover rats after repeated application of silver sulfadiazine cream (nanonized) for 28 consecutive days followed by 14 days recovery.

A total of 120 (60 males and 60 females) Wistar Hannover rats were received for the conduct of the study. Out of these, a total of 68 rats (34 males and 34 females) were selected for toxicity study (main and recovery study) and a total of 42 rats (21 males and 21 females) were selected for toxicokinetics study. The selected animals were randomly distributed into four groups (Groups I, II, III and IV). For the toxicity study, each group of the main study consisted of 6 animals/sex and additionally 5 animals/sex were allotted to Groups I and IV as recovery animals. For toxicokinetic study, each group consisted of 6 animals/sex, except Group I, which consisted of 3 animals/sex. The mean group body weight of the animals, distributed to various dose groups, did not differ statistically on the day of randomization.

The amount of cream applied for all the animals was 1000 mg/kg/day. The placebo for silver sulfadiazine cream (nanonized) was applied to animals belonging to Group I; whereas silver sulfadiazine cream (nanonized) with the concentration of 2.5% w/w, 5% w/w, and 10% w/w corresponding to doses of 25, 50, and 100 mg/kg/day of silver sulfadiazine was applied to animals belonging to Group II, III, and IV, respectively, for 28 consecutive days. The recovery animals were provided 14 days of treatment free recovery period.

Observations comprised of mortality, clinical signs, ophtalmoscopy, body weight, feed consumption, hematology, clinical chemistry, and urine analysis. All survived rats were euthanized on day 29 (main study animals) and on day 43 (recovery animals), using carbon dioxide asphyxiation and were examined for gross pathological lesions. Microscopic examination of tissues/organs was carried out for Group I [placebo for silver sulfadiazine cream (nanonized); dose of 0 mg/kg/day] and Group IV [10% w/w silver sulfadiazine cream (nanonized); dose of 100 mg/kg/day] of the main study. Additionally, gross lesions of all the animals and all the tissues of animals found dead were also examined irrespective of dose group.

Blood samples for toxicokinetics evaluation were collected on day 1 and day 28 at predose (Group I on day 1 and day 28; Groups II, III, and IV on day 28), 1 hour±5 minutes, 3 hours±5 minutes, 6 hours±5 minutes, 10 hours±5 minutes, and 24 hours±5 minutes post dosing. Plasma samples were processed by liquid-liquid extraction and analyzed for sulfadiazine using a non validated LC-MS/MS method. The silver estimation was carried out by using ICPMS in a non GLP domain.

No treatment related mortality or clinical signs were noted in either sex up to 100 mg/kg/day of silver sulfadiazine. Likewise, no treatment related changes in mean body weight, percent change in body weight with respect to day 1, ophthalmoscopy, hematology, clinical chemistry, organ weight and urine analysis were observed in either sex up to 100 mg/kg/day of silver sulfadiazine (nanonized).

No treatment related gross pathological or histopathological changes were noticed in either sex at 100 mg/kg/day of silver sulfadiazine (nanonized).

Based on these findings, it was concluded that, under the prevailed experimental conditions, the No Observed Adverse Effect Level (NOAEL) of silver sulfadiazine cream (nanonized) in Wistar Hannover rats, after dermal application on abraded skin for 28 consecutive days followed by 14 days of treatment free recovery period, was 100 mg/kg/day.

Clinical Study

An open-label, randomized, pilot study was carried out to compare the efficacy, safety, and tolerability of silver sulfadiazine cream (nanonized) and marketed Silverex® cream in the prophylaxis of infection in burn wounds.

Testing protocol specifications and a detailed time and events schedule were prepared to assure consistent execution of the protocol throughout the study. Subjects were screened to ensure that they met the inclusion and exclusion criteria. This was a randomized, open-label, comparative, parallel-group, three-arm, multicentric pilot study of 6 weeks duration. Treatment with the study medication was continued until the wounds healed or up to a period of 21 days, whichever was earlier. A thin layer of study medication [0.5% w/w, or 0.75% w/w silver sulfadiazine cream (nanonized) or 1.0% w/w Silverex® cream] sufficient to cover the wounds was applied, once daily in cases of closed dressing and twice daily in cases of open dressing. All subjects were called for a safety follow up assessment on day 42. During the study period, subjects were assessed 5 times: 'Treatment period' (assessment 1 on day 0, assessment 2 on day 7, assessment 3 on day 14, and assessment 4 on day 21) and a 'Safety follow-up' assessment (assessment 5 on day 42).

A total of 40 subjects were randomized in this study [14 subjects in the silver sulfadiazine cream (nanonized) 0.5% w/w; 12 subjects in the silver sulfadiazine cream (nanonized) 0.75% w/w; and 4 subjects in the Silverex® cream 1.0% w/w group]. The study population consisted of 4 (28.6%), 8 (66.7%) and 11 (78.6%) male subjects and 10 (71.4%), 4 (33.3%), and 3 (21.4%) female subjects in the silver sulfadiazine cream (nanonized) 0.5% w/w, silver sulfadiazine cream (nanonized) 0.75% w/w, and Silverex® cream 1.0% w/w groups, respectively. Analysis population was classified into three groups:

Intent to Treat (ITT)
  ITT population included all randomized subjects who had applied the study medication and had at least one post application efficacy assessment.
Per Protocol (PP)
  Per protocol population included all randomized subjects who completed the study treatment as per protocol.
Safety Population
  Safety population included all randomized subjects who had applied the study medication at least once and had at least one post-application safety assessment.

Efficacy parameters and safety measures were the criteria for evaluation. The primary efficacy parameter was the proportion of subjects with wound infection during the study treatment period. The clinical diagnosis of infection was as per judgment of the investigator based on symptoms and signs that included purulent drainage, erythema, warmth, exudation, malodor, pain, and/or fever. The secondary efficacy parameters were: a) proportion of subjects achieving complete wound closure by day 21; b) proportion of subjects achieving complete wound closure by day 14; and c) proportion of subjects achieving complete wound closure by day 7. Safety assessments included recording of adverse events, vital signs (pulse rate, systolic and diastolic blood pressure, body temperature, and respiratory rate), physical examination, and clinical laboratory investigations (hematology, biochemistry and urinalysis). Adverse events were classified according to their seriousness, severity and relationship to the study treatment. Any clinically significant abnormal change from baseline in the concurrent medical condition(s), physical examination, and/or laboratory data was also recorded as an adverse event.

Results

At the end of the treatment period (21 days), in the PP population none of the subjects had wound infection in the three treatment groups. In the ITT population, one subject each in the three treatment groups [7.7% in both the silver sulfadiazine cream (nanonized) 0.5% w/w group and Silverex® cream 1.0% w/w group and 8.3% in the silver sulfadiazine cream (nanonized) 0.75% w/w group] was considered to have wound infection during the treatment period. The difference was not statistically significant [P-value between groups i.e., silver sulfadiazine cream (nanonized) vs. Silverex® 1.0% w/w group: >0.999]. Therefore, the three study treatments were equally effective in preventing infection in patients with partial thickness thermal burns.

With respect to wound closure by day 7, the proportion of subjects achieving wound closure was comparable in the 3 treatment groups in both PP and ITT population. Two subjects (16.7%) in the silver sulfadiazine cream (nanonized) 0.5% w/w group and none of the subjects in the silver sulfadiazine cream (nanonized) 0.75% w/w or Silverex® 1.0% w/w group achieved complete wound closure by day 7 in the PP population. The differences were not statistically significant. Similar results were observed in the ITT population.

With respect to wound closure by day 14, the proportion of subjects achieving wound closure was comparable in the 3 treatment groups in both PP and ITT population. Five subjects (41.7%), 4 subjects (36.4%), and 1 subject (9.1%) in the silver sulfadiazine cream (nanonized) 0.5% w/w, silver sulfadiazine cream (nanonized) 0.75% w/w, and Silverex® 1.0% w/w group respectively achieved complete wound closure by day 14 in the PP population. The differences were not statistically significant. Similar results were observed in the ITT population.

With respect to wound closure by day 21, the proportion of subjects achieving wound closure was comparable in the 3 treatment groups in both PP and ITT population. Eleven subjects (91.7%) in the silver sulfadiazine cream (nanonized) 0.5% w/w, 11 subjects (100%) in silver sulfadiazine cream (nanonized) 0.75% w/w, and 6 subjects (54.5%) in Silverex® cream 1.0% w/w group in the PP population achieved complete wound closure by day 21. Similar results were observed in the ITT population. The difference between sulfadiazine cream (nanonized) 0.75% w/w and Silverex® cream 1.0% w/w group were found to be statistically significant.

With respect to safety results, a total of 7 adverse events were reported in two subjects during the course of the study. Of the 7 AEs, 6 AEs were reported in one subject (7.7%) in the Silverex® 1.0% w/w group. The subject recovered completely without sequelae from these adverse events during the course of the study. One AE was reported in one subject (8.3%) in the silver sulfadiazine cream (nanonized) 0.75% w/w group. The outcome of this adverse event is 'Unknown' as the subject did not return for AE follow up. The reported adverse events were considered 'unlikely' to be related to the study medication and were 'mild' or 'moderate' in intensity. No 'serious' adverse events were reported during the study period. None of the subjects were withdrawn from the study due to adverse events. There were no important changes in vital signs, physical examination, or clinical laboratory evaluations from baseline, in any of the treatment groups during this study. Overall, the safety profile of the three study medications was similar.

Based on the results of the efficacy and safety parameters, silver sulfadiazine cream (nanonized) 0.5% w/w and 0.75% w/w appear to be as effective and equally safe as Silverex® cream 1.0% w/w in the prophylaxis of infection in burn wounds.

The invention is further illustrated by the following non-limiting examples.

EXAMPLES

Silver Sulfadiazine (Nanonized Cream)

| Ingredients | Qty (% w/w) | | | | |
| --- | --- | --- | --- | --- | --- |
|  | Example 1 | Example 2 | Example 3 | Example 4 | Example 5* |
| Part A: Silver Sulfadiazine Slurry (Nanonized) | | | | | |
| Silver Sulfadiazine | 0.10 | 0.25 | 0.50 | 0.75 | 1.00 |
| Hydrogen Peroxide Solution | 0.02 | 0.05 | 0.10 | 0.15 | 0.20 |
| Polyvinyl pyrrolidone | 0.10 | 0.10 | 0.10 | 0.10 | 0.10 |
| Sodium metabisulphite | 0.05 | 0.05 | 0.05 | 0.05 | 0.05 |
| Purified Water | 40.00 | 40.00 | 40.00 | 40.00 | 40.00 |
| Part B: Drug | | | | | |
| Chlorhexidine Gluconate Solution eq to Chlorhexidine | 0.20 | 0.20 | 0.20 | 0.20 | 0.20 |
| Part C: Oil Phase | | | | | |
| Cetostearyl Alcohol | 9.60 | 9.60 | 9.60 | 9.60 | 9.60 |
| Cetomacrogol 1000 | 2.50 | 2.50 | 2.50 | 2.50 | 2.50 |

-continued

| Ingredients | Qty (% w/w) | | | | |
|---|---|---|---|---|---|
| | Example 1 | Example 2 | Example 3 | Example 4 | Example 5* |
| Light Liquid Paraffin | 8.00 | 8.00 | 8.00 | 8.00 | 8.00 |
| Butylated Hydroxytoluene | 0.10 | 0.10 | 0.10 | 0.10 | 0.10 |
| Part D: Water Phase | | | | | |
| Purified Water | 30.00 | 30.00 | 30.00 | 30.00 | 30.00 |
| Disodium Edetate | 0.01 | 0.01 | 0.01 | 0.01 | 0.01 |
| Chlorocresol | 0.10 | 0.10 | 0.10 | 0.10 | 0.10 |
| Part E | | | | | |
| Phosphoric Acid | q.s. | q.s. | q.s. | q.s. | q.s. |
| Sodium phosphate | q.s. | q.s. | q.s. | q.s. | q.s. |
| Purified Water | q.s. to 100 g | q.s. to 100 g | q.s. to 100 g | q.s. to 100 g | q.s. to 100 g |

*Particle size of silver sulfadiazine in the formulation was determined using Zetasizer with water as dispersant, and the Z-average particle size was found to be 465 nm.

BRIEF MANUFACTURING PROCEDURE

Preparation of Part A
1. Hydrogen peroxide and sodium metabisulphite were dissolved in purified water.
2. Polyvinyl pyrrolidone was dispersed into the bulk of step 1.
3. Silver sulfadiazine was mixed into the mixture.
4. The slurry was passed through a Dynomill and collected and the Dynomill was rinsed with purified water.
5. The slurry and rinsing were used in the fabrication of the cream.

Preparation of Cream
1. The oil phase was prepared by mixing together cetostearyl alcohol, cetomacrogol 1000, light liquid paraffin, and butylated hydroxytoluene and heating to 65° C. to 70° C.
2. The water phase was prepared by heating purified water to 65° C. to 70° C. and dissolving disodium edetate and chlorocresol in it.
3. The oil phase was added slowly under homogenization to the water phase to form an emulsion, which was then cooled under stirring.
4. Chlorhexidine gluconate was added and mixed into the bulk of step 3.
5. Silver sulfadiazine slurry and the rinsing were added and mixed into the bulk of step 4.
6. The pH was adjusted to 6 using phosphoric acid and sodium phosphate.
7. Final weight adjustment was done using purified water followed by mixing.

| Ingredients | Qty (% w/w) | |
|---|---|---|
| | Example 6 | Example 7 |
| Part A: Silver Sulfadiazine Slurry (Nanonized) | | |
| Silver Sulfadiazine | 1.00 | 1.00 |
| Hydrogen Peroxide Solution | — | 0.10 |
| Polyvinyl Pyrrolidone | 0.10 | 0.10 |
| Sodium Metabisulphite | — | — |
| Purified Water | 40.0 | 40.00 |
| Part B: Drug | | |
| Chlorhexidine Gluconate Solution eq to Chlorhexidine | 0.20 | 0.20 |
| Part C: Oil Phase | | |
| Cetostearyl Alcohol | 9.60 | 9.60 |
| Cetomacrogol 1000 | 2.50 | 2.50 |

-continued

| Ingredients | Qty (% w/w) | |
|---|---|---|
| | Example 6 | Example 7 |
| Light Liquid Paraffin | 8.00 | 8.00 |
| Butylated Hydroxytoluene | 0.10 | 0.10 |
| Part D: Water Phase | | |
| Purified Water | 30.00 | 30.00 |
| Disodium Edetate | 0.01 | 0.01 |
| Chlorocresol | 0.10 | 0.10 |
| Part E | | |
| Phosphoric Acid | q.s. | q.s. |
| Sodium Phosphate | q.s. | q.s. |
| Purified Water | q.s. to 100 g | q.s. to 100 g |

Formulations 6 and 7 were prepared in the same manner as described above, except omitting the step of addition of hydrogen peroxide and sodium metabisulphite in Example 6 and excluding sodium metabisulphite addition in Example 7.

The formulations of examples 5, 6 and 7 were evaluated with regards to effect of various antioxidants on product stability. The results of the stability studies are compiled in Table 6.

TABLE 6

| Observations of Stability study | | |
|---|---|---|
| S No. | Formulation | Observations on stability |
| 1. | Example 5 | No color change observed on stability |
| 2. | Example 6 | SSN slurry became black immediately |
| 3. | Example 7 | Samples became black on stability |

From the above results it is evident that a combination of hydrogen peroxide and sodium metabisulfite is effective in preventing any color change of silver sulfadiazine in the pharmaceutical composition.

| INGREDIENTS | Quantity (mg/g) | |
|---|---|---|
| | Example 8 (0.5% w/w) | Example 9 (0.75% w/w) |
| Silver Sulfadiazine | 5.37 | 8.06 |
| Chlorhexidine Gluconate Solution equivalent to Chlorhexidine Gluconate | 10.75 | 10.75 |
| Povidone | 1.00 | 1.00 |
| Sodium Metabisulphite | 1.00 | 1.00 |

-continued

| INGREDIENTS | Quantity (mg/g) | |
|---|---|---|
| | Example 8 (0.5% w/w) | Example 9 (0.75% w/w) |
| Hydrogen Peroxide Solution | 4.00 | 5.00 |
| Cetostearyl Alcohol | 96.00 | 96.00 |
| Cetomacrogol 1000 | 25.00 | 25.00 |
| Light Liquid Paraffin | 80.00 | 80.00 |
| Butylated Hydroxytoluene | 1.00 | 1.00 |
| Disodium Edetate | 0.10 | 0.10 |
| Sodium Phosphate | q.s. | q.s. |
| Phosphoric Acid | q.s. | q.s. |
| Purified Water | q.s. to 1.00 g | q.s. to 1.00 g |

BRIEF MANUFACTURING PROCEDURE

1. Disodium edetate, a portion of hydrogen peroxide solution, and a portion of sodium metabisulphite were dissolved in a portion of purified water.
2. Povidone was dispersed into the bulk of step 1 under stirring.
3. Silver sulfadiazine was dispersed in the bulk of step 2 under stirring.
4. The dispersion of step 3 was milled by wet grinding process using Dynomill and the milled slurry was collected in a vessel.
5. The remaining portion of sodium metabisulphite was dissolved in a portion of purified water and the Dynomill was rinsed using this solution.
6. The rinsing was separately collected in a vessel.
7. Cetostearyl alcohol, cetomacrogol 1000, and light liquid paraffin were heated to melt and were mixed together.
8. Butylated hydroxytoluene was added to the melt of step 7.
9. The water phase was transferred to the main mixing vessel and stirred continuously.
10. The oil phase of step 7 was added to the aqueous phase in the main mixing vessel under high speed stirring until a homogenous emulsion was formed.
11. The bulk of step 10 was cooled and the remaining portion of hydrogen peroxide solution with purified water was added and mixed well.
12. The rinsing from step 6 were added into the bulk of step 11 and mixed well.
13. Chlorhexidine gluconate solution was prepared in purified water and added to the bulk of step 12.
14. The pH of the ointment was checked and adjusted to 6.0 using 0.5% w/w solution of phosphoric acid in purified water or 5% w/w solution of sodium phosphate in purified water.
15. The final weight of the ointment was made up using purified water.

We claim:

1. A dose-reduced topical pharmaceutical composition consisting of 0.5% w/w of nanonized silver sulfadiazine and 0.2% w/w chlorhexidine gluconate, and one or more pharmaceutically acceptable excipients selected from the group consisting of thickening agents, emulsifying agents, preservatives, chelating agents, pH modifiers, coloring agents, perfumes, and antioxidants, wherein the topical pharmaceutical composition exhibits a similar efficacy when compared to a marketed composition containing 1.0% w/w micronized silver sulfadiazine.

2. The topical pharmaceutical composition of claim 1, wherein the efficacy is determined by:
    a) proportion of patients achieving complete wound closure by day 21 of the treatment period; or
    b) microbial log reduction of *Pseudomonas aeruginosa* count in thermal injury model in rats.

3. The topical pharmaceutical composition of claim 2, wherein the application of the nanonized composition to patients leads to complete wound closure by day 21 of treatment period in at least 90% of the total patient population.

4. The topical pharmaceutical composition of claim 2, wherein the microbial log reduction of *Pseudomonas aeruginosa* count in a thermal injury model in rats using the topical pharmaceutical composition is comparable to that caused by the composition containing 1.0% w/w micronized silver sulfadiazine.

5. The topical pharmaceutical composition of claim 1, wherein the thickening agent is selected from one or more of soft paraffin, aluminum stearate, cetostearyl alcohol, propylene glycol, polyethylene glycols, povidone, wool-fat, hydrogenated lanolin, or beeswax.

6. The topical pharmaceutical composition of claim 1, wherein the emulsifying agent is selected from one or more of cetomacrogol, non-ethoxylated glyceryl monostearate, carbopols, cetearyl alcohol, sodium stearoyl lactylate, or lecithin.

7. The topical pharmaceutical composition of claim 1, wherein the chelating agent is selected from one or more of dimercaprol, ethylene diamine tetra acetic acid (EDTA), ethylene glycol tetraacetic acid, deferoxamine, or alfa lipoic acid.

8. The topical pharmaceutical composition of claim 1, wherein the pH modifier is selected from one or more of citric acid, sodium citrate, acetic acid, sodium acetate, phosphoric acid, sodium phosphate, borax, or sodium hydroxide.

9. The topical pharmaceutical composition according to claim 1, wherein the composition is in the form of a cream, lotion, ointment, or gel.

10. The topical pharmaceutical composition of claim 1, wherein the nanonized silver sulfadiazine and chlorhexidine gluconate are the sole active therapeutic agents in the composition.

11. A dose-reduced topical pharmaceutical composition comprising of 0.5% w/w of nanonized silver sulfadiazine and one or more pharmaceutically acceptable excipients selected from the group consisting of thickening agents, emulsifying agents, preservatives, chelating agents, pH modifiers, coloring agents, perfumes, and antioxidants, wherein the topical pharmaceutical composition exhibits a similar efficacy when compared to a marketed composition containing 1.0% w/w micronized silver sulfadiazine.

* * * * *